United States Patent
Bijjani (10) Patent No.: US 7,362,847 B2
(45) Date of Patent: Apr. 22, 2008

(54) DISPLACED-RAY CT INSPECTION

(75) Inventor: Richard Robehr Bijjani, Cambridge, MA (US)

(73) Assignee: Reveal Imaging Technologies, Bedford, MA (US)

( * ) Notice: Subject to any disclaimer, the term of this patent is extended or adjusted under 35 U.S.C. 154(b) by 0 days.

(21) Appl. No.: 11/609,661

(22) Filed: Dec. 12, 2006

(65) Prior Publication Data
US 2007/0133744 A1  Jun. 14, 2007

Related U.S. Application Data

(60) Provisional application No. 60/749,807, filed on Dec. 12, 2005.

(51) Int. Cl.
*G01N 23/04* (2006.01)

(52) U.S. Cl. .............................. 378/57; 378/9

(58) Field of Classification Search .................. 378/57, 378/15, 19, 14, 4, 9
See application file for complete search history.

(56) References Cited

U.S. PATENT DOCUMENTS

| 5,195,112 A | 3/1993 | Vincent et al. ............. 378/10 |
| 6,229,870 B1 * | 5/2001 | Morgan ......................... 378/9 |
| 2003/0219092 A1 * | 11/2003 | Bressel et al. ............... 378/4 |
| 2005/0167601 A1 | 8/2005 | Bruder et al. ............. 250/367 |
| 2005/0232390 A1 | 10/2005 | Bruder et al. ............. 378/19 |
| 2006/0078085 A1 * | 4/2006 | Zanker ....................... 378/57 |
| 2006/0245548 A1 * | 11/2006 | Callerame et al. ......... 378/160 |
| 2006/0274883 A1 * | 12/2006 | Buck et al. ................. 378/57 |

FOREIGN PATENT DOCUMENTS

EP  1 177 767 A2  2/2002

OTHER PUBLICATIONS

International Search Report for PCT/US2006/047547, mailed on May 22, 2007.

* cited by examiner

*Primary Examiner*—Hoon Song
(74) *Attorney, Agent, or Firm*—Mintz, Levin, Cohn, Ferris, Glovsky and Popeo, P.C.

(57) ABSTRACT

A computed tomography scanner includes a housing, a conveyor disposed at least partially within the housing and configured to move an object to be scanned through the housing along a direction of travel, a gantry connected to the housing and configured to receive the object to be scanned, an x-ray source attached to the gantry and configured to provide an x-ray beam that extends along a length in the direction of travel, and detector arrays attached to the gantry and configured and disposed to receive and detect x-rays from the x-ray source, the detector arrays being displaced relative to each other in the direction of travel an array spacing distance such that a geometric efficiency of the arrays is less than about 80%.

18 Claims, 12 Drawing Sheets

PRIOR ART

| Det. 1 | Det. 2 | Det. 3 | Degrees |
|---|---|---|---|
| 0 | | | 0 |
| 2.5 | 0 | 90 | 60 |
| 5 | 2.5 | 0 | 120 |
| 7.5 | 5 | 2.5 | 180 |
| 10 | 7.5 | 5 | 60 |
| 12.5 | 10 | 7.5 | 120 |
| 15 | 12.5 | 10 | 0 |

DISPLACED-RAY CT INSPECTION

CROSS-REFERENCE TO RELATED ACTIONS

This application claims the benefit of U.S. Provisional Application No. 60/749,807 filed Dec. 12, 2005, which is incorporated herein by reference.

BACKGROUND

Security checkpoints, such as those located in airports, screen people and packages for contraband, such as weapons or explosives. Various technologies are used at such checkpoints. Typically, individuals pass through metal detection devices. Projection x-ray systems screen baggage and packages. In current conditions of heightened security, passengers can experience long delays in passing through security checkpoints. For baggage, an operator typically reviews all images of screened baggage to determine whether the baggage includes contraband. A typical operator receives extensive training to recognize certain types of objects in an x-ray image. Furthermore, a typical operator receives training to distinguish objects layered within the bags from a single two dimensional x-ray image.

In addition to individuals and carry-on baggage, checked bags are also now scanned at airports. Generally, in the United States, the Transportation Security Administration (TSA) uses computed tomography (CT) scanning for checked bags. CT scanners create a three dimensional image of a bag which allows better differentiation of objects relative to projection x-ray systems. Explosive detection system (EDS) designers specifically developed and deployed CT scanners for the detection of explosives.

Figure 1:
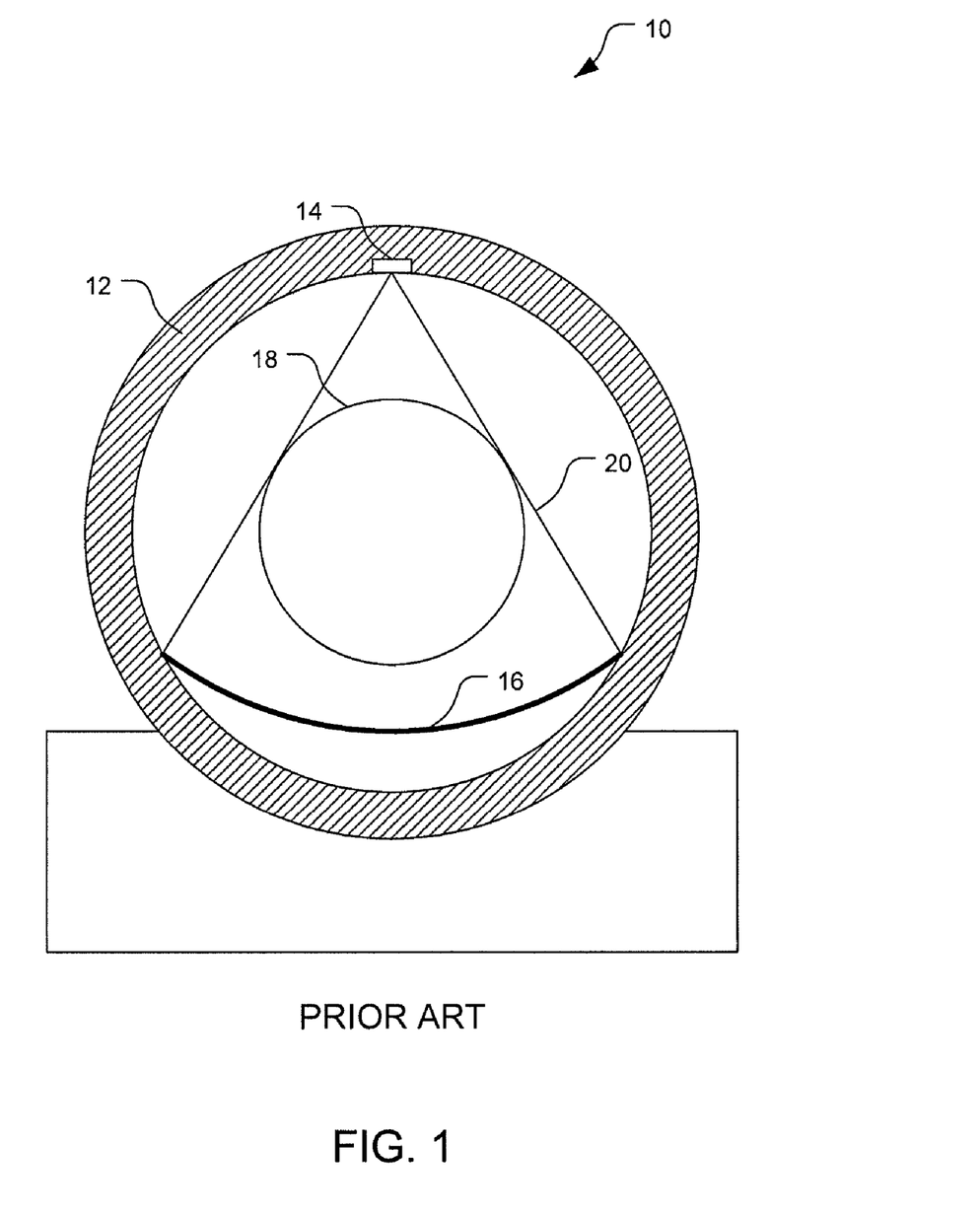
FIG. 1 is a cross-sectional view of a conventional CT scanner taken in a plane perpendicular to motion of an object to be scanned by the scanner.

As noted above, CT technology is effective for explosive detection. CT machines typically incorporate a rotating ring or "gantry" on which the X-ray source and detectors are mounted. Referring to FIG. 1, a CT scanner 10 typically includes a gantry 12, an x-ray source 14, and a detection device 16. The gantry 12 surrounds a tunnel 18 through which baggage may pass. A conveyor (not shown) can move baggage through the tunnel 18 for scanning. The gantry 12 can rotate about the tunnel 18, and the detection device 16 can collect slices of data. The x-ray source 14 is configured to produce a narrow angle beam 20. The detection device 16 is positioned on the gantry 12 to intersect the x-ray beam 20 passing through the tunnel 18. The detection device 16 comprises multiple x-ray detectors that are typically located at equal distances from the x-ray source 14. The x-ray source 14 and the detection device 16 are sized and positioned so that the entire tunnel 18 falls within the x-ray beam 20. The data from the detection device 16 can be analyzed by a computer to generate a three-dimensional representation of the contents of the bag in the tunnel 18.

Conventional CT scanning and reconstruction used in baggage inspection is slow and cumbersome. Two known methods for CT scanning, i.e., helical and axial. In helical scanning, the detection device includes multiple detection devices disposed adjacent to each other in the direction of travel of the object under inspection, e.g., a bag, and the object is continuously moved through the scanner. The object is moved slowly (but faster than in axial CT) so that a collection of x-ray detectors readings (or interpolation of readings) could be assembled for each rotation which would substantially appear to be from a single plane. The bag is moved approximately the length (up to twice the length) of the multiple detection devices for each rotation. In transaxial CT scanning, the object under inspection is periodically stopped and a single slice is scanned. The object is then moved a short distance, stopped, and scanned again. Both of these processes result in slow movement of baggage through the scanner. Once the data have been collected, the data are reconstructed to create a three dimensional representation of the baggage. From the three dimensional representation, individual items are reviewed as possible threats. The three dimensional representation, or slices of it, may also be displayed for review by an operator.

The TSA has recognized the need to improve the security process at the passenger checkpoint, such as by using checkpoint EDS. Using conventional EDS at the checkpoint, however, could worsen throughput at already crowded security checkpoints. The TSA and airports are struggling to keep up with passenger loads using today's passenger screening systems and procedures. Lines up to 2 hours can form during peak periods and will likely get worse as TSA headcount is further reduced and passenger loads increase.

SUMMARY

In general, in an aspect, the invention provides a computed tomography scanner including a housing; a conveyor disposed at least partially within the housing and configured to move an object to be scanned through the housing along a direction of travel; a gantry connected to the housing and configured to receive the object to be scanned; an x-ray source attached to the gantry and configured to provide an x-ray beam that extends along a length in the direction of travel; and detector arrays attached to the gantry and configured and disposed to receive and detect x-rays from the x-ray source, the detector arrays being displaced relative to each other in the direction of travel an array spacing distance such that a geometric efficiency of the arrays is less than about 80%.

Implementations of the invention may include one or more of the following features. The array spacing distance is such that a geometric efficiency of the arrays is less than about 70%, less than about 60%, less than about 50%, less than about 40%, less than about 30%, or less than about 20%. The array spacing is such that if the conveyor moves the object in the direction of travel at a first speed and the gantry rotates at a second speed, the object will move a distance substantially equal to the array spacing distance during a time that the gantry rotates an angle approximately equal to 180° divided by a quantity of the detector arrays.

In general, in another aspect, the invention provides a computed tomography scanner including a housing; a conveyor disposed at least partially within the housing and configured to move an object to be scanned through the housing along a direction of travel; and an x-ray transmission and detection system connected to the housing and configured and disposed to transmit at least one x-ray fan beam through the object on the conveyor with x-rays displaced along the length of travel passing through the object, the x-ray transmission and detection system being further configured to detect x-rays in the at least one fan beam after passing through the object, the detected x-rays being displaced along the direction of travel when passing through the object; where the detected x-rays passing through the object are displaced relative to each other in the direction of travel to provide an effective geometric efficiency of the detected x-rays that is less than about 80%.

Implementations of the invention may include one or more of the following features. The transmission and detection system includes at least one source and at least two detector arrays, or at least two sources and at least one detector array. If the transmission and detection system includes at least one source and at least two detector arrays, then the detector arrays are sampled sequentially, and if the transmission and detection system includes at least two sources and at least one detector array, then the sources are excited sequentially. The transmission and detection system includes at least one detector array with detectors disposed substantially completely 360° around the conveyor. The transmission and detection system includes x-ray sources disposed substantially completely 360° around the conveyor. The transmission and detection system includes detectors having detector widths and pairs of x-ray sources with sources in the pairs being displaced relative to each other approximately one-half of the detector width in a direction substantially perpendicular to the direction of travel. The transmission and detection system is configured such that the effective geometric efficiency is less than about 60%, less than about 40%, or less than about 20%. The x-ray transmission and detection system includes x-ray sources and the x-ray transmission and detection system is configured to trigger the sources at different energies to capture multi-energy data for atomic number calculations.

In general, in another aspect, the invention provides a method of CT scanning an object, the method including moving the object along a direction of travel; transmitting displaced x-rays through the object substantially perpendicular to the direction of travel; detecting the displaced x-rays with an effective geometric efficiency at the object of about 80% or less; combining information indicative of detected intensities of the displaced x-rays to group information from different x-rays for common slices together; and analyzing the combined information for slices of the object.

In accordance with implementations of the invention, one or more of the following capabilities may be provided. Passenger baggage can be screened for explosives while with improved passenger throughput compared to use of conventional EDS. A faster CT EDS scanner can be provided, and can be provided without increasing the size of CT EDS scanners with similar detection devices, and without increasing gantry rotation rate. CT scan speed may be proportional to a quantity of detector arrays disposed in a direction of travel of a scanned object. A CT scanner could run at speeds that far exceed those of Helical CT scanners with similar axial image resolution and number of detector elements, or at similar speeds and at a fraction of the cost of detector elements and associated electronics and computer requirements of Helical CT scanners.

These and other capabilities of the invention, along with the invention itself, will be more fully understood after a review of the following figures, detailed description, and claims.

DETAILED DESCRIPTION OF PREFERRED EMBODIMENTS

Embodiments of the invention provide techniques for CT scanning objects, e.g., scanning airline checked or carry-on baggage for explosives. For example, a CT EDS scanner includes an x-ray source mounted to a gantry, a conveyor for moving the object to be scanned relative to the gantry, and multiple detector arrays disposed along a direction of travel of the object to be scanned. The detector arrays are separated from each other a substantial distance. For example, a distance between leading edges (i.e., edges nearest an entry point of objects into the scanner) of adjacent detector arrays is approximately equal to two times a desired slice thickness. This scanner is exemplary, however, and not limiting of the invention as other implementations in accordance with the disclosure are possible.

Figure 2:
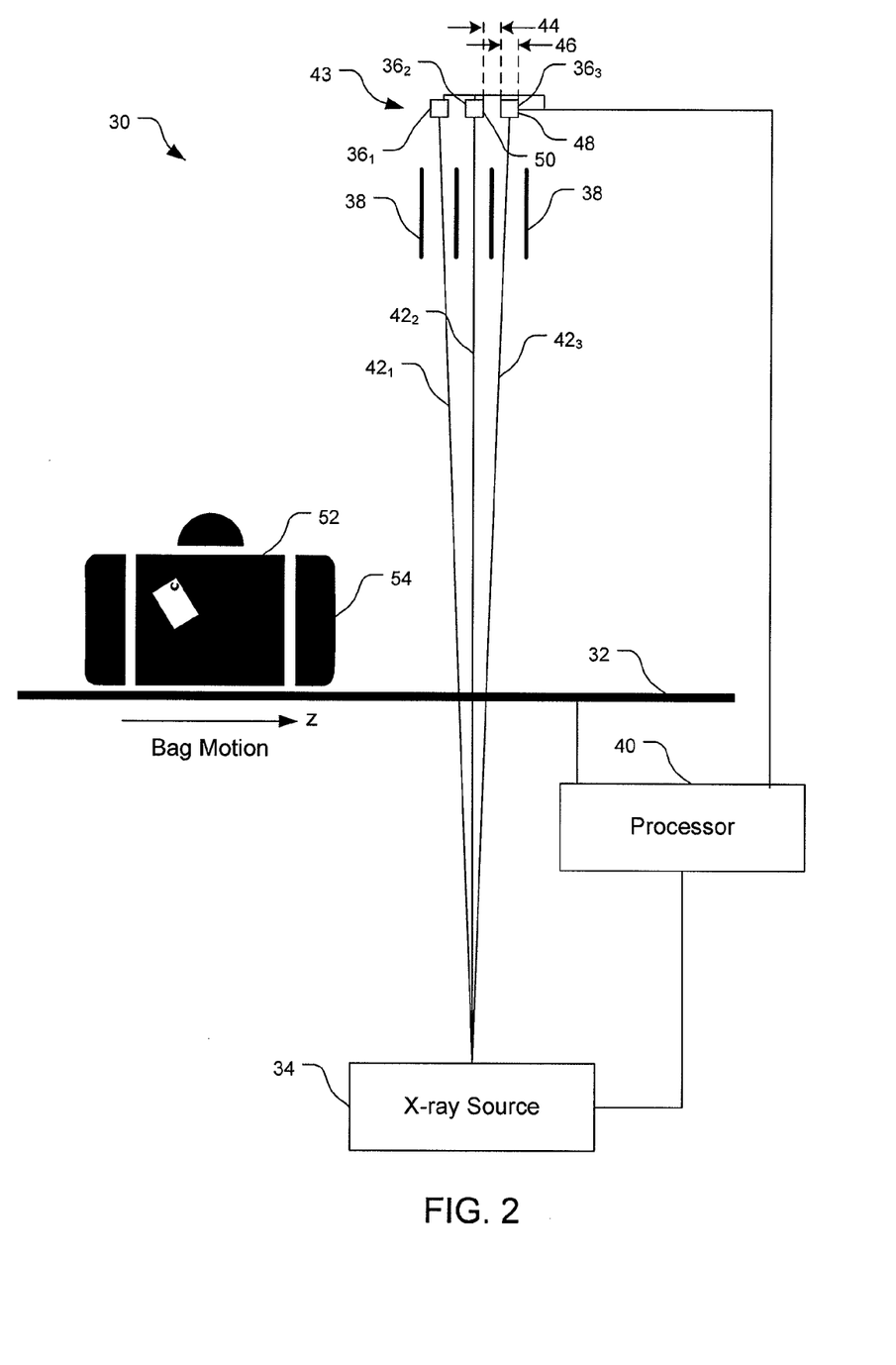
FIG. 2 is a schematic diagram of components of a CT scanner using multiple rows of detector arrays spaced apart from each other.
Figure 3A:
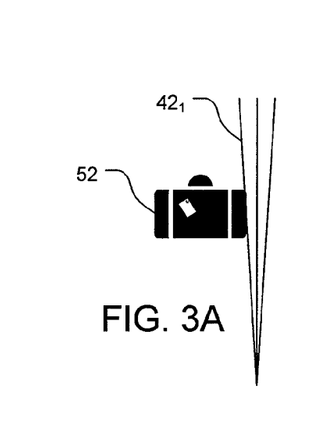
FIGS. 3A, 3C, 3E are schematic diagrams of an object being scanned using the scanner shown in FIG. 2 at three different positions relative to an x-ray beam provided by the scanner, corresponding to three different scanning instances while the object is moving through the scanner.
Figure 3B:
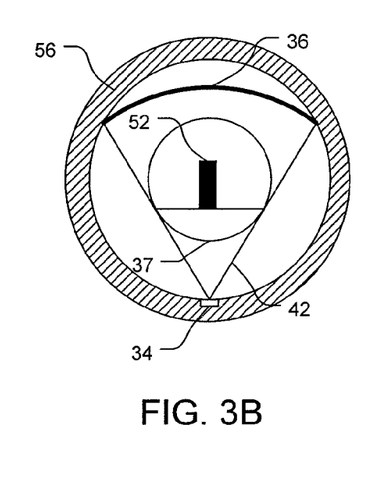
FIGS. 3B, 3D, 3F are cross-sectional views of the scanner shown in FIG. 2 at the three different times of FIGS. 3A, 3C, 3E, with a gantry of the scanner rotating to three different corresponding positions.
Figure 3C:
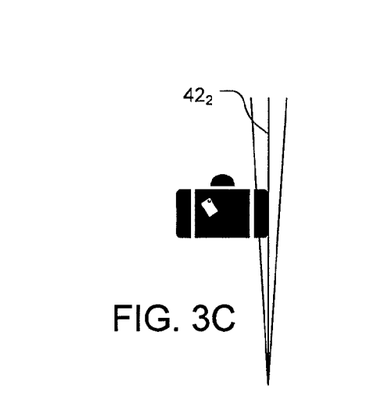
Figure 3D:
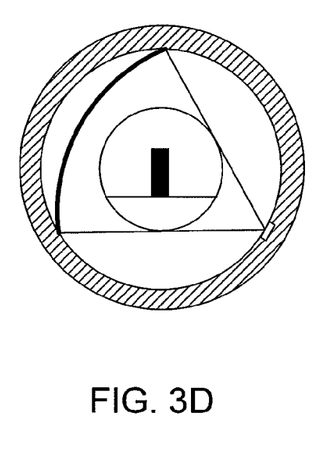
Figure 3E:
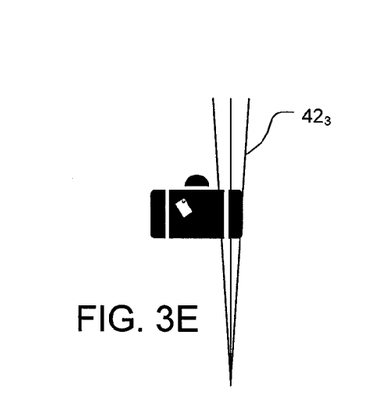
Figure 3F:
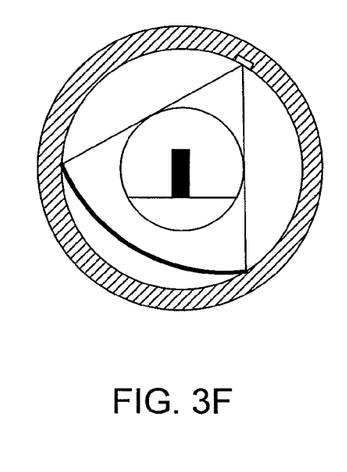

Referring to FIG. 2, a CT scanner 30 includes a conveyor 32, an x-ray source 34, detector arrays 36, anti-scatter plates 38, and a processor 40. The scanner 30 includes other items that are not shown. The optional anti-scatter plates 38 are disposed along a direction of travel z of an object under inspection 52 and are configured to limit the x-ray scatter in the conveyor motion direction z to reduce reception of x-rays by the detector arrays $36_1$-$36_3$ that scatter off items in the object under inspection 52 not in a direct line between the source 34 and the respective detector array 36. For example, the plates 38 may be made of tungsten. The source 34 is configured to provide an x-ray beam 42 that is a fan beam in a plane orthogonal to the direction z of travel of the object 52 that encompasses a tunnel 37 (FIG. 3) of the scanner 30 (similar to the beam shown in FIG. 1). The beam 42 has width in the z-direction such that beam portions $42_1$-$42_3$ are received by the detector arrays $36_1$-$36_3$, respectively. The processor 40 includes memory for storing computer-readable software instructions for controlling components of the scanner 30 to perform functions as described herein. The detector arrays 36 can be of various configurations such as the configuration of the detection device 16 shown in FIG. 1, or the set of detector arrays 240, 241, 242 shown in FIGS. 3-4 of U.S. Application Publication No. 2004/0120454. These examples are not limiting of the forms that the detector arrays 36 may take. The scanner 30 is a third generation CT scanner (i.e., with a tunnel of the scanner being fully intersected by a beam 42 provided by the source 34), although other types of scanners may be used. The scanner 30 is configured to scan objects at faster rates than with a scanner using a single detector array 36. Here, the scanner 30 includes three detector arrays 36, although other quantities of detector arrays 36 may be used. Preferably, however, if a large number of detector arrays 36 are used, more than one x-ray source 14 could be used, e.g., disposed adjacent to the shown x-ray source 14 in the z-direction.

The detector arrays 36 are disposed in a set 43 and are separated from each other in the bag motion direction z, with gaps 44 between the arrays 36. The gaps 44 are substantial in relation to widths 46 of the detector arrays 36. For example, the gaps 44 may be larger than the widths 46. Preferably, a geometric efficiency of the detector array set 43, which is the width 46 of a detector array 36 divided by an array pitch (i.e., the distance between leading edges of adjacent arrays 36 (e.g., from a leading edge 48 of the array $36_3$ to a leading edge 50 of the array $36_2$)), times 100%, is preferably below 80%. The geometric efficiency could be less than 70%, less than 60%, less than 50%, less than 40%, less than 30%, or below 20%. Preferably, the geometric efficiency is less than 30%. The geometric efficiency of the scanner 30 is equal to an effective geometric efficiency of the scanner 30, the effective geometric efficiency being a projection of the detector arrays 36 along the beams 42 to an arbitrary plane between the arrays 36 and the source 34. The array pitch is preferably approximately equal to two times the desired slice thickness because the slice thickness is typically about half of the detector array pitch because the detector arrays 36 are disposed twice as far from the isocenter of rotation of the gantry 56 as is the object 52.

The processor 40 is configured to control the conveyor 32 to move the object under inspection 52, e.g., a piece of luggage, at a substantially constant linear speed and to control a gantry 56 (FIG. 3) to rotate at a substantially fixed rotational speed while the x-ray source 34 emits x-rays. The detector arrays 36 are configured to detect x-rays transmitted by the source 34 and attenuated by items in the bag 52, and transmit indications of the received x-rays to the processor 40. The processor 40 is configured to use the indications of received x-ray amounts to identify potential threats such as explosives, identify regions of the bag 52 containing potential threats, and to reconstruct images of the bag 52. The processor 40 is configured to use data from the detector arrays 36 for each half-revolution as a complete scan or slice.

The speed of the conveyor 32, and thus throughput of the scanner 30, depends upon the rotational speed, sampling rate and the number of detector arrays 36. For example, with n detector arrays 36, two slices per revolution of the gantry (i.e., 180° per slice), and the speed of the conveyor 32 such that the time it takes a leading edge 54 of the bag 52 to move from one beam portion, e.g., $42_1$, to the next, $42_2$, the gantry would have rotated 1/n of half a rotation (180/n degrees). Referring also to FIGS. 3A-F, the conveyor 32 will move the bag 52 from the beam portion $42_1$ to the beam portion $42_2$ as the gantry rotates ⅓ of 180°, or 60°, and to the beam portion $42_3$ as the gantry rotates a total of 120°. Thus, the portion of the slice detected by each of the arrays is reduced to a third, and thus the speed of the conveyor can be increased by 3 times relative to a scanner using a single one of the detector arrays 36. Thus, if for one detector array 36 the conveyor 32 could be run at 7.5 cm/s, at a gantry rotational speed of 90 RPM, and with acceptable resolution, then with 4 arrays, the conveyor 32 could be run at 30 cm/s without sacrificing image or threat detection quality.

Figure 4:
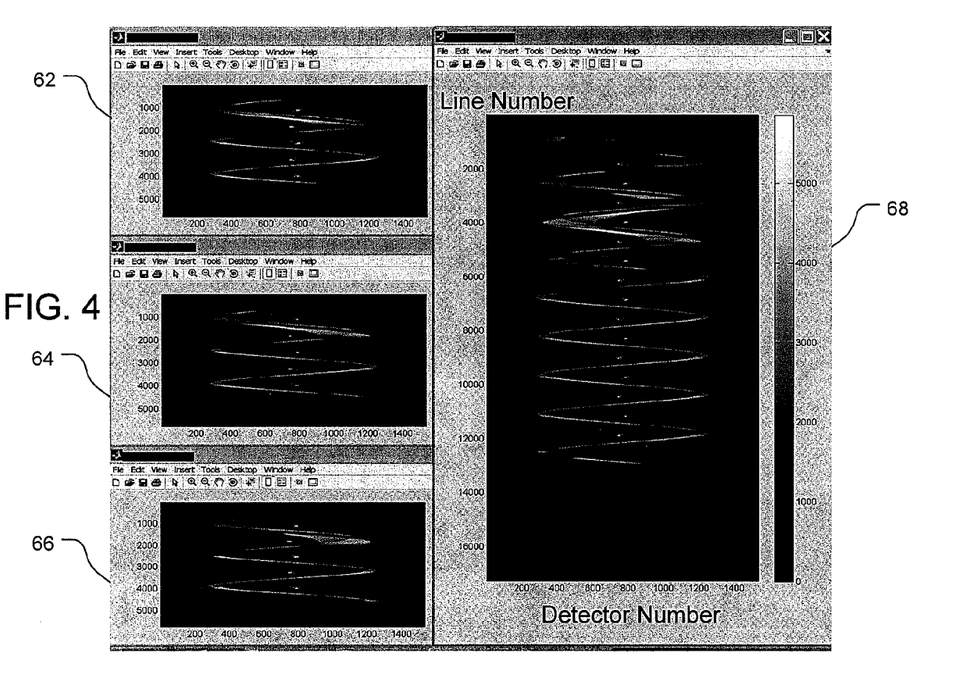
FIG. 4 is three graphs of information detected by the three detector arrays of the scanner shown in FIG. 2 as a function of time, and a graph of the combined information from the three graphs.
Figure 5:
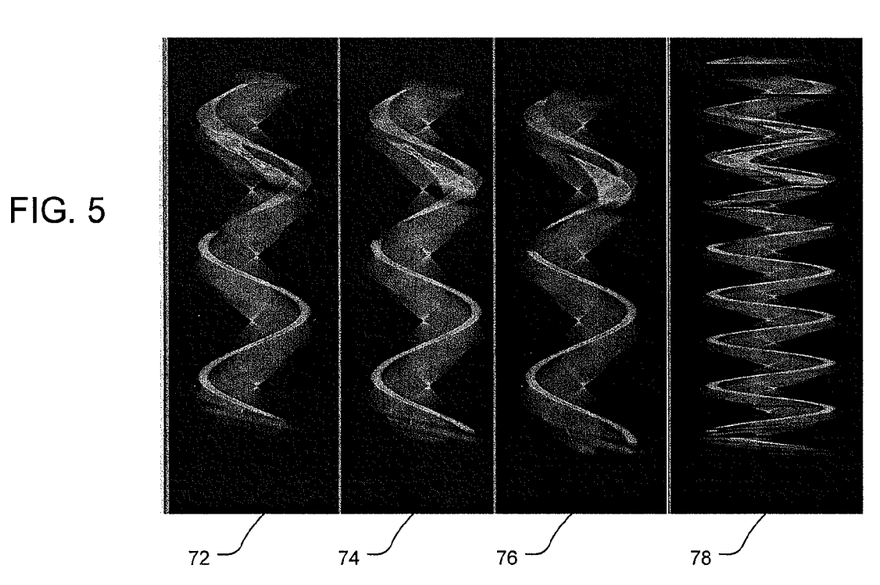
FIG. 5 is three graphs of information detected by the three detector arrays of the scanner shown in FIG. 2 as a function of distance traveled by an object under inspection, and a graph of the combined information from the three graphs.

The processor 40 is configured to use indications of received x-rays from each of the detector arrays 36 for each CT slice. Each detector array 36 will receive x-rays passing through each portion of the bag 52, but from different angles. The processor 40 is configured to combine the information from the arrays 36 for the same linear portion (i.e., the same slice in the z-direction), while accounting for the different angles at which the information is acquired. The processor 40 is configured to take the detector outputs from the detector arrays 36 and combines the information into one effective array. The combined effective array will have n times the sampling lines (views) as each of the individual arrays 36. Referring also to FIGS. 4-5, the processor 40 is configured to combine the information of graphs 62, 64, 66 provided by the arrays $36_1$-$36_3$, respectively, into the information in graph 68 of an effective array. In FIG. 4. the horizontal axes signify the detector number, the vertical axes represent the line number, and the shading signifies attenuation. The graphs 62, 64, 66 show the individual detector readings for each detector over all the sampling times. These graphs are known as lineograms (as described in U.S. Application Publication No. 2005/0008118 A1) and are similar to what is known as a sinogram in the industry. The combined lineogram 68 has n times the number of lines (n=3) compared to each of the number of lines in the graphs 62, 64, 66. In FIG. 5, vertical axes represent distance traveled by the bag 52 in the z-direction. Graphs 72, 74, 76 show that the travel distance is identical for the n arrays 36 and the combined lineogram 78. The combined lineogram 78 however, has more resolution in the bag motion direction z.

Figure 13:
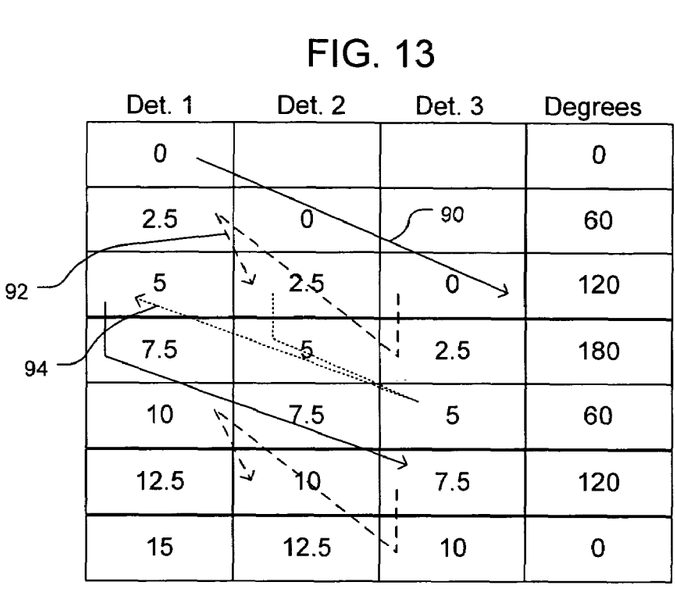
FIG. 13 is a table of a scheme to recombine information from the detector arrays.

Referring again to FIG. 2, the processor 40 is configured to implement a scheme illustrated in FIG. 13 to recombine information from the detector arrays 36 into one lineogram for the case of n=3. While FIG. 13 is for the case of n=3, similar tables can be produced for other values of n. The fan angle data for all n detector arrays 36 is parallelized and assumed to be parallel for this discussion. This is a convenient step and helps in understanding the process. By applying more cumbersome mathematics, however, the same could be accomplished using the fan data. The first column of FIG. 13 shows the distance z traveled by the bag 52 as measured from its leading edge 54. In this example, it is assumed that the conveyor 32 is moving the bag 52 at 15 cm/s as the gantry 54 rotates at 60 RPM. The gantry thus rotates 360° every second, and 180° every ½ second, equating to 7.5 cm of travel of the conveyor 32 and the bag 52 in ½ sec. For each detector array 36 to travel its share of the 180°, that is 180°/n, here 180°/3=60°, the conveyor 32 and the bag 52 will thus travel 7.5/n, here 7.5/3=2.5 cm. FIG. 13 is thus broken into segments corresponding to 60° of gantry rotation and 2.5 cm of corresponding motion of the conveyor 32 and travel of the bag 52.

FIG. 13 indicates how to 'knit' the data from the three arrays 36 into one effective array. The data for the one effective array will be similar to the data gathered by one detector array machine running at one third the speed of the three-array system 30. Again, the use of three arrays is for illustration purposes only and similar tables can be made for any number of arrays. In FIG. 13, the first column represents the data used to make the first recombined slice. Here we select the first 60° from array 1, the second 60° from detector array 2 and the third 60° from detector array 3 as indicated by a solid line 90. To recombine the data for the second slice, 60° of data are used from each the three detector arrays as indicated by a dashed line 92. The rule used is to start by using the last detector array used in the previous slice (in this case detector array 3). Next, data are used from the next 2 arrays, in this case detector array 1 then 2. The data are flipped (mirror image in the detector domain) to simulate the data coming from 180° away. For the third slice, as indicated by a dashed line 94, data are first used from the same array from which data were used for the end of slice 2, here detector array 2, then data are used from the next detector array, here the array 3, flipped and back to the first array. This process is repeated for all subsequent slices. The process could be interpreted as: Every 60 degrees worth of data, switch to the next detector array; after a sequence of nine switches (three full slices of the recombined data), the process repeats. The sequence is summarized as: Slice 1: Use 1, 2, 3; Slice 2: use 3, If, 2f; Slice 3: use 2f, 3f, 1. For all subsequent slices use the above scheme in a recurring pattern of three. For slice m, use the scheme in slice number X, where X=remainder of m/3. For example, for slice 20, use slice rem(20/3)=Slice 2 scheme. If m/3=0, then use scheme 3. Thus, for slice 12, use slice rem(12/3)=slice 0; thus, use the slice 3 scheme.

The detector arrays 36 collect x-rays passing through the same portion of the bag 52 at different times and different rotation angles of the gantry 56. In the first 60° of gantry rotation after the leading edge 54 of the bag 52 reaches the first beam portion $42_1$, the detector array $36_1$ collects x-rays passing through and attenuated by the first 2.5 cm of the bag 52. During the second 60°, the first detector array $36_1$ receives x-rays passing through the bag range of 2.5 to 5 cm, and so on. The detector arrays $36_2$ and $36_3$ also detect x-rays passing through these portions of the bag 52, except that the leading edge 54 of the bag 52 does not reach the second detector array $36_2$ until 2.5 cm more travel in the z-direction, or 60 degrees of gantry rotation. This 2.5 cm (15/2n) spacing corresponds to the separation of the fan beam portions 42 at the isocenter of the gantry 56, with the detector arrays 36 being separated by a distance of 15/n cm in the z or conveyor motion direction.

The processor 40 is configured to combine information from the detector arrays 36 to form a lineogram such that for every swath of 2.5 cm (or conveyor speed/2n, in general), the object 52 is inspected from at least 180°. For the first 0-2.5 cm swath of the bag 52, the first detector array $36_1$ provides information for the first 60°, the second array $36_2$ provides information for the angular rotation of 60° to 120°, and the third detector array $36_3$ provides information for 120° to 180°. For the second 2.5 cm displacement (slice), the information from the third detector $36_3$ is used for the range 180° to 240°. For the angular range of 240° to 300°, the processor 40 will use information from the first detector array $36_1$ again, but reverse the detector direction. The x-ray will be at angles 60°-120° (180° away from 240°-300°) when the second swath is being inspected by the first detector array $36_1$. Since the data will be taken from the opposite side of the gantry 56, the processor 40 is configured to compensate for this by interchanging or flipping left and right. Thus, to combine information from the arrays 36, the processor 40 is configured to use information for the 60° increments from the detector arrays 36 in the following order: $36_1$, $36_2$, $36_3$ for the first slice and every third ($n^{th}$) slice thereafter, $36_3$, $36_1(f)$, $36_2(f)$ for the second slice and every third slice thereafter, and $36_2(f)$, $36_3(f)$, $36_1$ for the third slice and every third slice thereafter, with (f) indicating a flip of the detector array readout. This pattern is summarized in FIG. 6. This pattern repeats for the remainder of the bag 52. Viewed another way, the information collected by the detector arrays 36 is used in as indicated in Table 1. Information from each portion of a rotation of the gantry 56 is used. Preferably, no collected information is discarded, but this is not required.

TABLE 1

Figure 6:
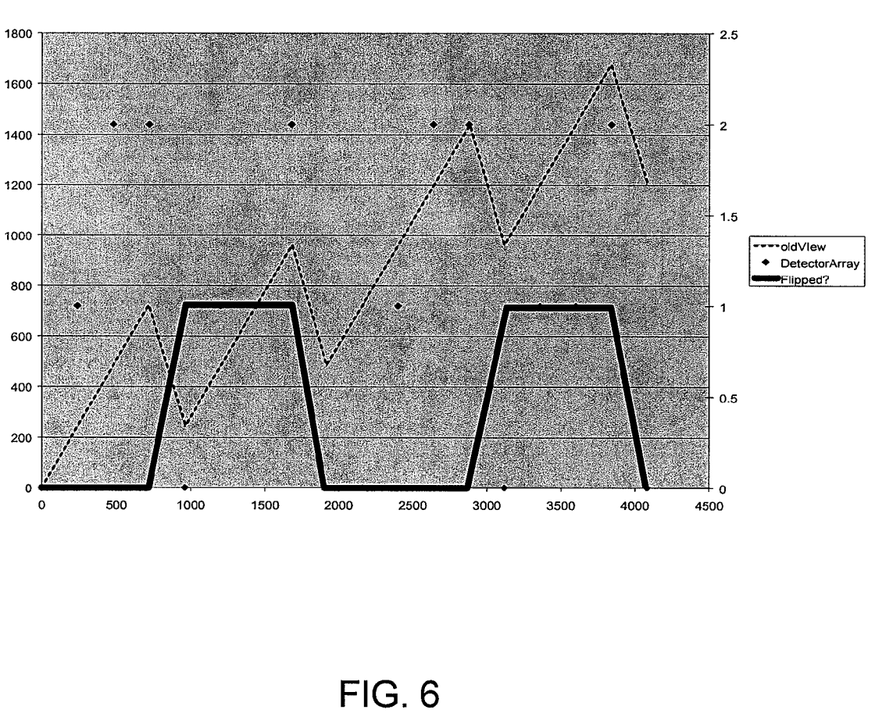
FIG. 6 is a graph of a scheme for combining information from the three detector arrays of the scanner shown in FIG. 2.

| Detector Array | Slice/Scan Number For 60° Increments | | |
| --- | --- | --- | --- |
| 1 | 1 | 2(f) | 3 |
| 2 | 1 | 2(f) | 3(f) |
| 3 | 1 | 2 | 3(f) |

Thus, information collected in the ranges 0°-60°, 60°-120°, and 120°-180° by the arrays $36_1$, $36_2$, $36_3$ is used in the first slice, the second slice, and the third slice, respectively, with information in the second slice from the first array $36_1$, information in the second and third slices from the second array $36_2$, and information in the third slice from the third array $36_3$ all being flipped. The data are flipped by taking the mirror image of each sample, where the first detector is treated as the last and the last as the first. Magnification correction is applied where appropriate, e.g., for objects that are relatively far away from the isocenter. This pattern repeats every three slices and continues for the remainder of the bag 52.

Figure 7:
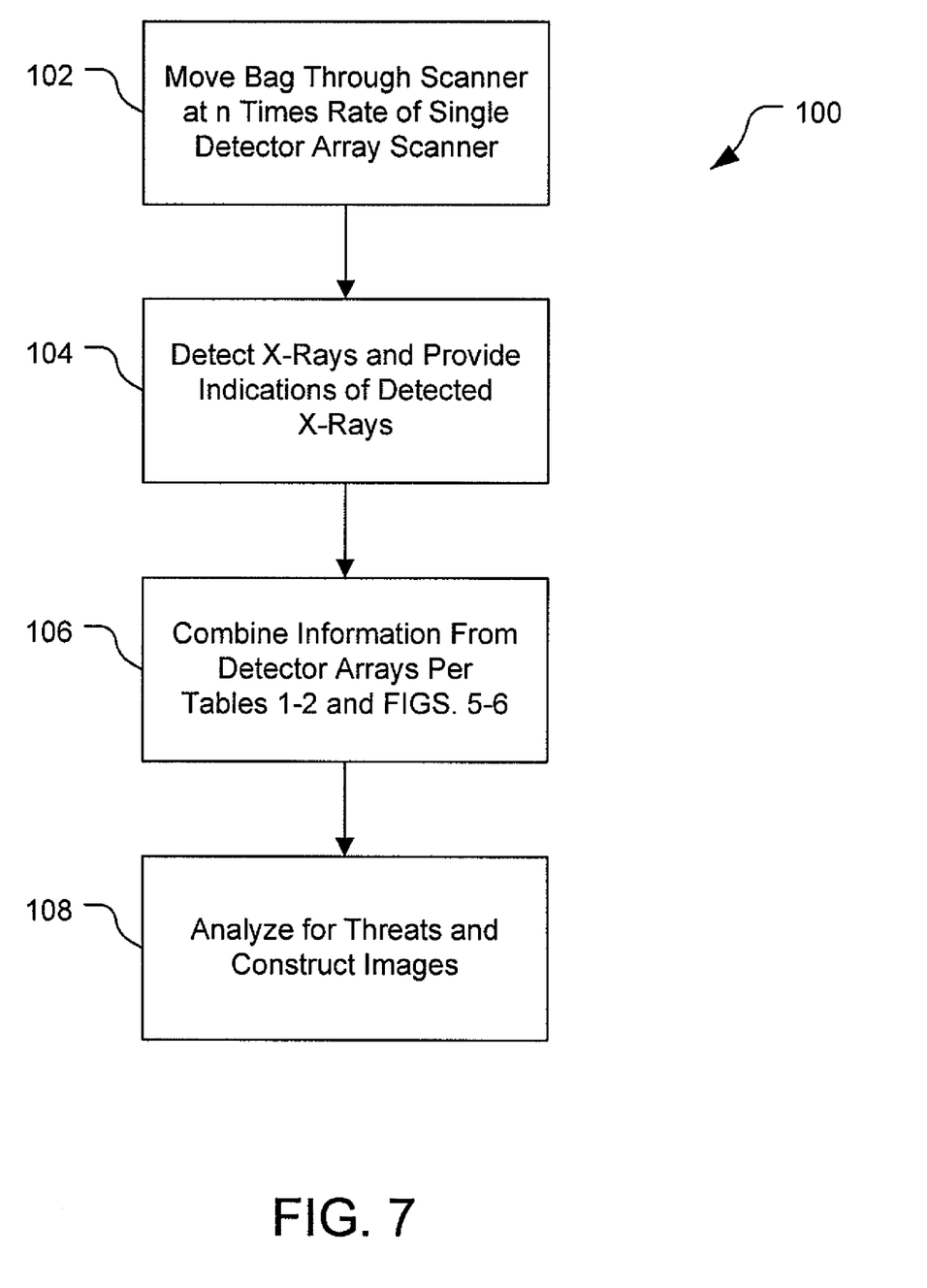
FIG. 7 is a block flow diagram of a process of acquiring and combining information of x-rays passed through an object under inspection by the scanner shown in FIG. 2.

In operation, referring to FIG. 7, with further reference to FIGS. 2-3, and 5-6, and Tables 1-2, a process 100 for acquiring and combining CT information using the scanner 30 includes the stages shown. The process 100, however, is exemplary only and not limiting. The process 100 may be altered, e.g., by having stages added, removed, or rearranged.

At stage 102, the bag 52 is moved though the field of view of the x-ray source 34 and the detector arrays 36. The bag 52 is placed on the conveyor 32, which is moved at a desired rate to move the bag 52 at a corresponding z-direction rate. The rate of the conveyor 32, and thus the bag 52 is preferably about n (here three) times the rate that would be used if a single detector array 36 was used.

At stage 104, x-rays from the source 34 are detected. The x-ray source 34 sends x-rays through the bag 52, that attenuates the x-rays, to the detector arrays 36. The x-rays are sent through the bag 52 with an effective geometric efficiency of less than about 80%, and preferably less than about 30%. The detector arrays 36 detect displaced transmitted x-rays, with the arrays 36 detecting x-rays sent through the same portion (i.e., z-direction linear position) of the bag 52 at different angles, here offset by 60° between successive detector arrays 36. The detector arrays 36 provide indications of the amounts of detected x-rays to the processor 40.

At stage 106, the processor 40 receives the indications of detected x-rays from the detector arrays 36 and combines these indications. The processor 40 combines the received indications in accordance with Tables 1-2 and FIGS. 5-6 to use the indications from the various detector arrays 36 for the appropriate slice, flipping the detected indications as appropriate. This assembles information for slices that yield information corresponding to a single detector array and conveyor speed, but with a much higher conveyor speed actually used.

At stage 108, the processor 40 uses the combined slice information to perform further desired functions. The processor 40 analyzes the combined slice information to identify potential threats such as explosives. The processor 40 also constructs images where appropriate, e.g., if an item in the bag 52 cannot be positively considered a threat or positively considered not to be a threat. The processor 40 provides the image information to an appropriate device for display to a human operator.

EXPERIMENTAL RESULTS

Figure 8A:
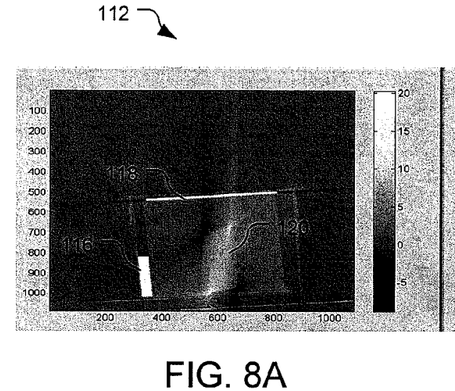
FIG. 8A is a graph of an image constructed from data from a single detector array of the scanner shown in FIG. 2.
Figure 8B:
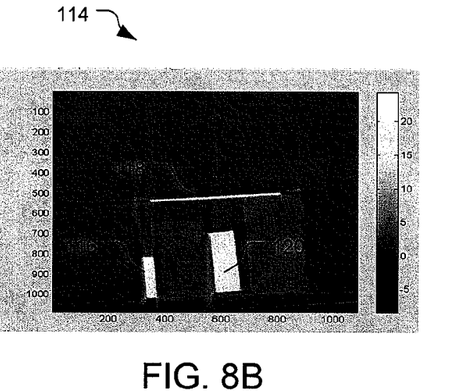
FIG. 8B is a graph of an image constructed from data from the three detector arrays of the scanner shown in FIG. 2.

Reconstructed lineograms using the combined information from three detector arrays has been shown to provide good image resolution. Referring to FIGS. 8A-8B, images 112, 114 of an actual bag containing three items illustrate image quality using the scanner 30 and the process 100, with a linear speed of the conveyor 32 of 15 cm/s. The bag contained a long block 116 of plastic (to the left in each of the images 112, 114). The block 116 was long enough to help ensure that even at 15 cm/s, its image could be reconstructed. A long thin piece 118 of plastic was placed near a top of the bag. A block in the middle of the bag was a 5 cm diameter plastic cylinder 120, standing up in the direction of motion. The reconstruction image 112 from the first detector array shows a very fuzzy shadow of the object 120. In the image 114 constructed using the combined information from the three detector arrays 36, the object 120 is in focus.

OTHER EMBODIMENTS

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations. Also, while the description above focused on the use of an x-ray source and multiple detector arrays, other arrangements may be used. For example, multiple x-ray sources and multiple x-ray detector arrays may be used together, or a single detector array and multiple x-ray sources may be used. Further, scanners may be used without anti-scatter devices. Anti-scatter plates in could also be used in the plane orthogonal to the z-direction, i.e., in the fan beam 42 from the source 34. Also, the invention described here could also work for other than a typical $3^{rd}$ generation CT. For example it could be applied to a broken array configuration as in the CT-80 CT EDS made by Reveal Imaging Technologies, Inc. of Bedford, Mass., or in a horse-shoe compact CT as described in U.S. Pat. No. 5,912,938 (Dobbs). Further, inventive techniques described here (both above and below) can be applied to $4^{th}$ generation systems with the detector array(s) spanning essentially the full 360° of the gantry (i.e., the full 360° around the conveyor, thus surrounding an object under test) and remaining stationary, or $5^{th}$ generation systems with no gantry used and the x-ray source(s) moved electronically around the field of view (e.g., with x-ray sources disposed around the conveyor and sequentially triggered to provide, effectively, a rotating x-ray source). Further still, the sources used can be nano-technology (nano-tube) x-ray sources.

Figure 9:
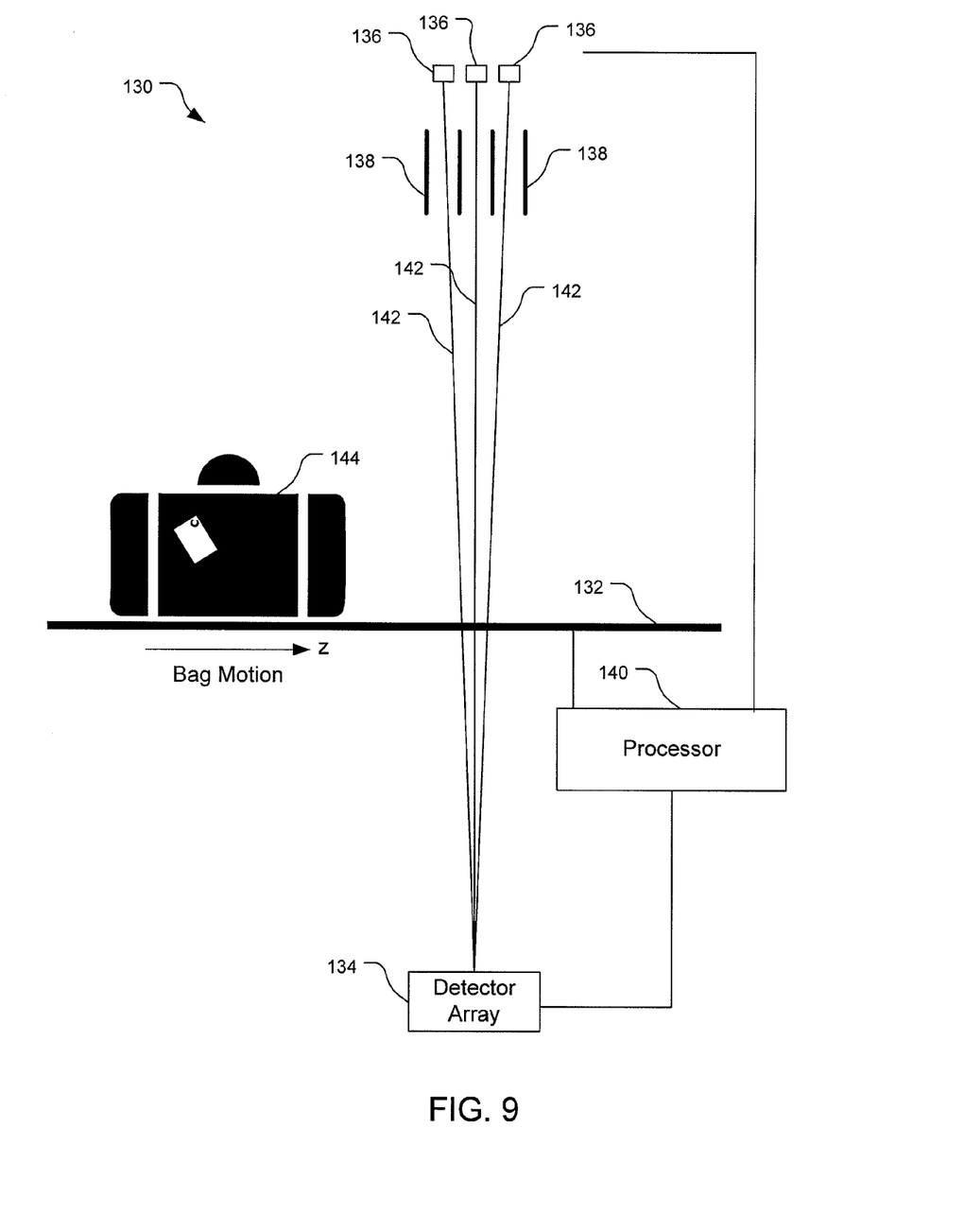
FIG. 9 is a schematic diagram of components of a CT scanner using one detector array and multiple x-ray sources spaced apart from each other.

Referring to FIG. 9, a CT scanner system 130 includes a conveyor 132, a detector array 134, a set of x-ray sources 136, anti-scatter plates 138, and a processor 140. The scanner system 130 includes other items that are not shown. The anti-scatter plates 138 are disposed along a direction of travel z of an object under inspection 144 and are optional. The sources 136 are configured to provide x-ray beams 142 that are fan beams in a plane orthogonal to the direction z of travel of the object 144. Here, there are three sources 136 and thus three x-ray beams 142, although other quantities may be used. With N sources 136, the sources 136 are controlled by the processor 140 to fire in succession at N times the sampling rate of a single-source/single-detector combination for equivalent resolution. Also, to help maintain the flux at a level approximately equal to the flux if a combination of one source and one detector array was used, the x-ray sources 136 are each controlled to provide N times the amount of photons used by a single source to provide equivalent image signal-to-noise values. This can be done by driving the sources 136 with increased voltage or, preferably, by driving the sources 136 with N times the amount of cathode current. Having flux (photons incident on the detector in a sampling period) equivalent to the single-detector and single-source case helps ensure an equivalent noise in the resulting image. Further, the sources 136 can be excited sequentially and at different energies to facilitate determination of atomic number by the processor 140. An effective geometric efficiency of the system 130, which is the geometric efficiency of the detector array 134 projected along the multiple beams 142 to an arbitrary plane (e.g., at the object 144 or the conveyor 132), is similar to that of the scanner 30 (i.e., preferably less than 30% but can be of various values as discussed above with respect to the scanner 30).

Figure 10:
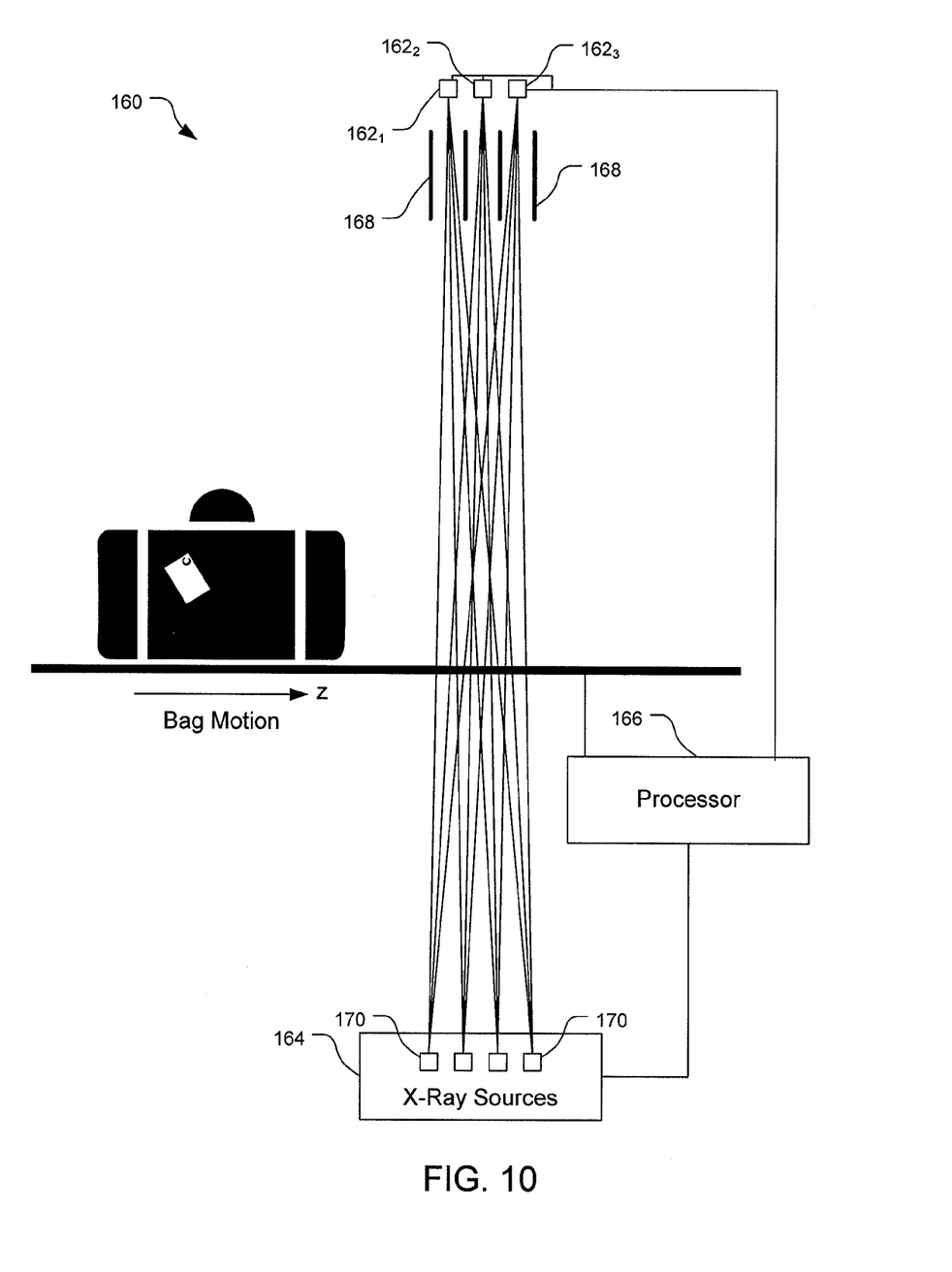
FIG. 10 is a schematic diagram of components of a CT scanner using multiple detector arrays and multiple x-ray sources spaced apart from each other.

Referring to FIG. 10, a CT system 160 includes detector arrays 162, a set 164 of x-ray sources, a processor 166, and optional anti-scatter plates 168. Here, the system 160 includes three detector arrays 162 and four x-ray sources 170. X-rays from each source 170 are incident upon each detector array 162. The sources can be fired sequentially or concurrently and the detector arrays 162 can be sampled sequentially or concurrently to capture data for explosives detection. Preferably, at data capture times, four data captures occur, either from the four sources 170 and one detector array 162 or the four arrays 162 and one source 170. Preferably, the sources 170 are excited sequentially because this uses less energy than having the sources 170 excited constantly and sequentially sampling the detector arrays 162. If more than four data captures occur simultaneously, e.g., all four sources 170 being excited and all four detector arrays 162 being sampled, then the "extra" data may be used to provide increased functionality, e.g., to provide more detailed three-dimensional images than if fewer data captures occur. An effective geometric efficiency of the system 160, which is the geometric efficiency of the detector arrays 162 if multiple arrays 162 are used to capture x-rays from one source, or one of the arrays 162 projected along the beams from the sources to an arbitrary plane is similar to that of the scanner 30 (i.e., preferably less than 30% but can be of various values as discussed above with respect to the scanner 30).

Figure 11:
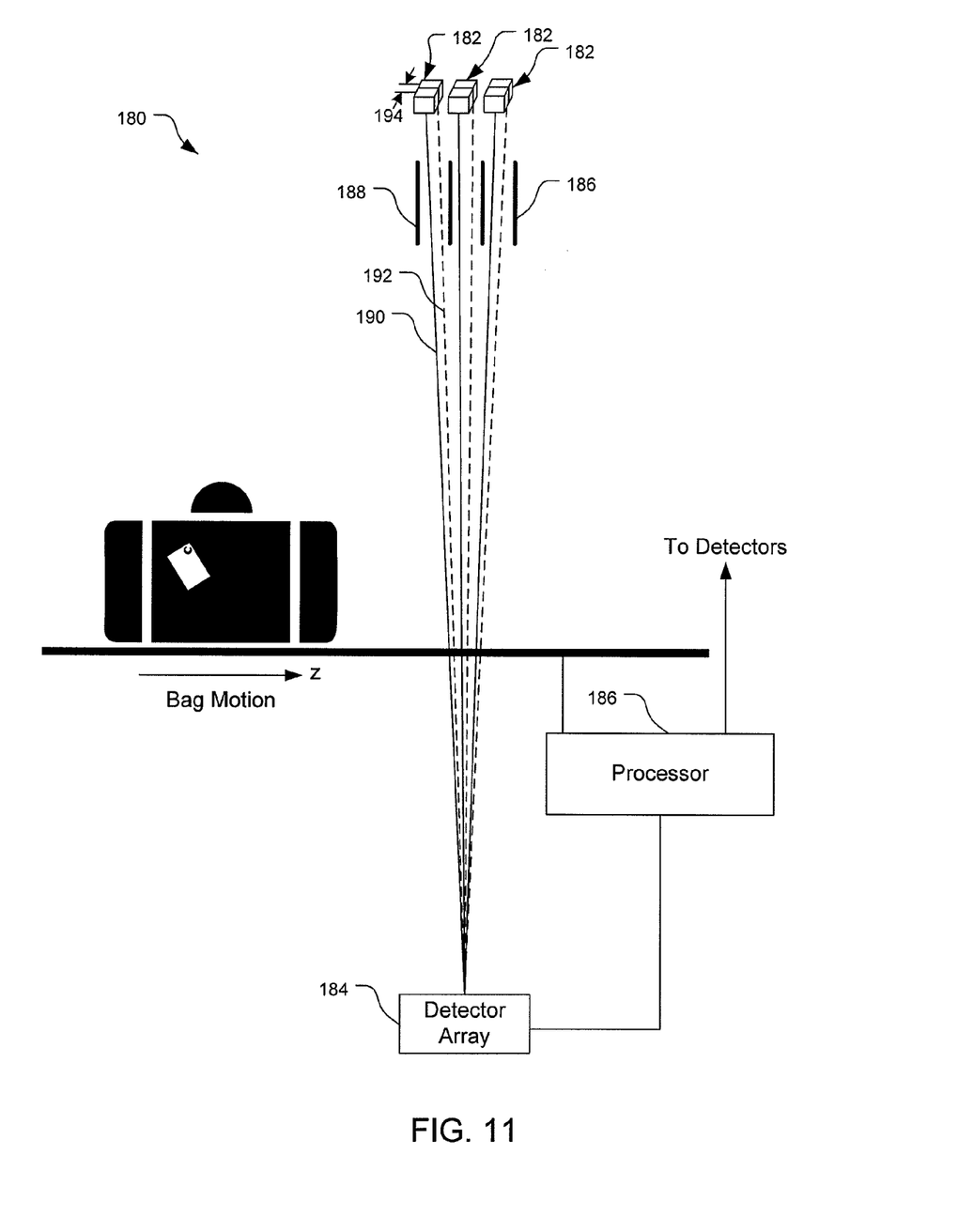
FIG. 11 is a schematic diagram of components of a CT scanner using one detector array and multiple pairs of x-ray sources spaced apart from each other.

Referring to FIG. 1, a CT system 180 configured to implement Quarter Shift Offset (QSO) (or quarter detector shift) image reconstruction includes pairs of x-ray sources 182, a detector array 184, a processor 186, and optional anti-scatter plates 188. Here, sources in the source pairs 182 provide two x-ray beams 190, 192 and are coplanar in the z-direction and have center-to-center spacings 194 in the plane of the x-ray fan beams (perpendicular to bag travel), of about one-half of a width of the detectors (detector pitch) in the array 184. The beams 190, 192 are incident upon the detector array 184 offset from each other as shown. The processor 186 controls the sources to emit x-rays from the sources in each pair in an alternating fashion, at 2N times (here 6 times) the rate for a single detector array, single source system. Using the system 180, captured x-ray information can be interlaced to appear as if there are twice as many detectors as there actually are in the array 184 with every 180° of rotation of a gantry on which the detector array 184 and the sources 182 are mounted (as opposed to 360° for QSO typically). Further, each of the pairs of sources 182 can have the two sources providing different energies to facilitate determination of atomic number by the processor 186. An effective geometric efficiency of the system 180, which is the geometric efficiency of the detector array 184 projected along the multiple beams 190, 192 to an arbitrary plane, is similar to that of the scanner 30.

Figure 12A:
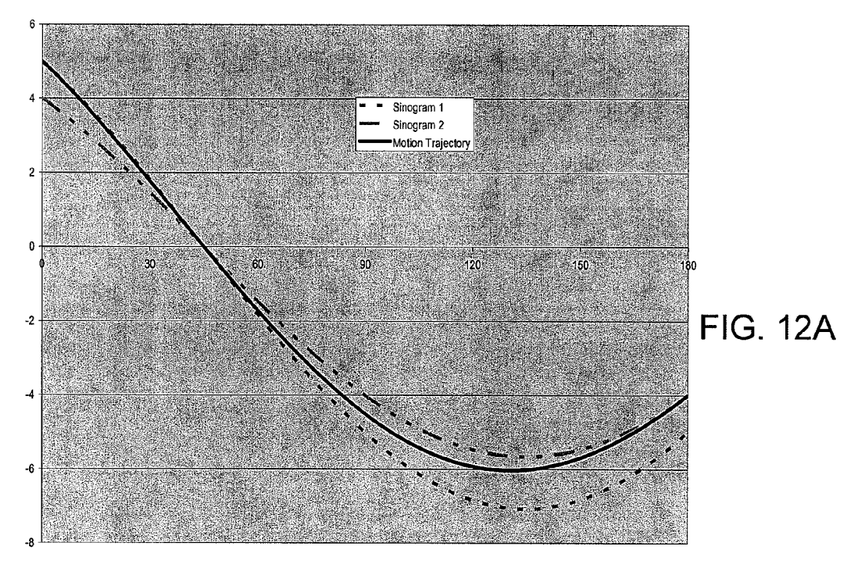
FIGS. 12A-12B are graphs showing a trajectory of a center of mass of an object under inspection for a one-detector array and one source system and for a multi-detector, multi-source system.
Figure 12B:
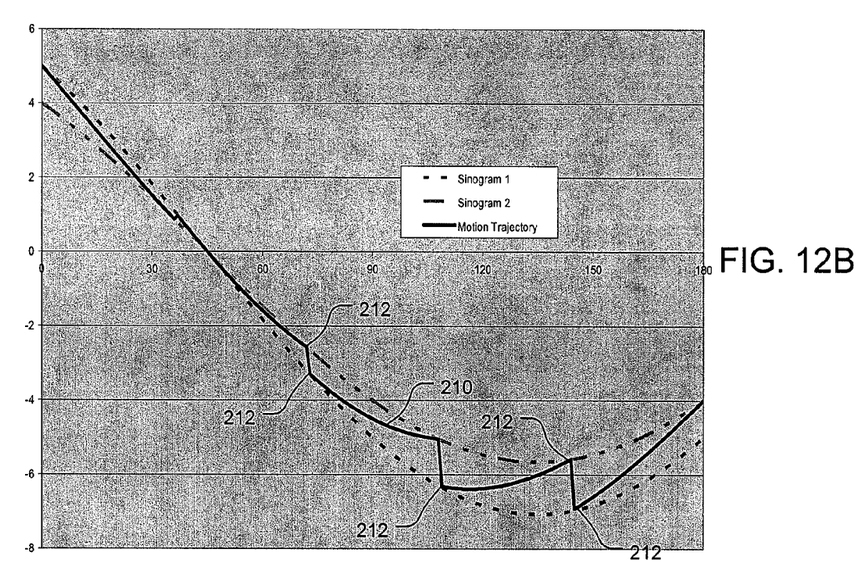

Information from multiple capture angles through the object under test can be processed to help correct artifacts. The multiple capture angles can be due to multiple detector arrays and/or multiple sources. If the object under test, or a portion thereof, (e.g., a parcel, a patient's hand, a patient's heart) moves during a single rotation of the detector(s)/source(s), then the trajectory of motion does not follow the theoretical sinogram. For example, referring to FIG. 12A, if an object moves from position 1 to position 2 in the course of a rotation, then the trajectory (lineogram) is not the sinogram spanned by position 1 and not the sinogram spanned by position 2, but appears as if it starts at sinogram 1 and ends at sinogram 2. For a clear image, the object trajectory should coincide with a sinogram trace. If the object does not so coincide, then the resulting image will be blurry. This image can be "snapped" back from blurry to sharp as described in U.S. patent application Ser. No. 11/417,692, Publication No. 2006/01984495 A1. Using multiple capture angles for the x-ray information, the "snapping" of the image from blurry to sharp is facilitated. Referring to FIG. 12B, using a system with multiple detector arrays and/or multiple sources, here five detector arrays, yields a plot for a moving object that is easily analyzed to determine data points to be used to sharpen an image. In FIG. 12B, there are easily-identifiable trajectory discontinuities 212 in a plot 210 corresponding to a moving object under test. The discontinuities can be used as anchor points of starting and end points in accordance with the description in U.S. 2006/01984495 A1 to manipulate the information to coincide with a sinogram, resulting in a sharp, high-resolution image.

The scanners 130, 160, 180 can be operated using the same principles as for the operation of the scanner 30. The object under inspection is impinged with displaced x-rays from one or more x-ray sources and the displaced x-rays are affected by the object and captured by one or more detector arrays. The captured energy is analyzed, to group data from slices together, and processed, e.g., to produce images, identify explosives, provide atomic numbers of items in the object, etc.

Still further embodiments are within the scope of the invention. For example, while the discussion above typically discussed three x-ray sources and/or three detector arrays, other quantities of sources and arrays, such as five x-ray sources and/or five detector arrays, may be used. Also, while the description and figures provided an example of a piece of luggage as an object under inspection, other objects may be inspected, such as a person or other animal.

Further, while the description above refers to the invention, the description may include more than one invention.

What is claimed is:

1. A computed tomography scanner comprising:
   a housing;
   a conveyor disposed at least partially within the housing and configured to move an object to be scanned through the housing along a direction of travel;
   a gantry connected to the housing and configured to receive the object to be scanned;
   an x-ray source attached to the gantry and configured to provide an x-ray beam that extends along a length in the direction of travel;
   a plurality of detector arrays attached to the gantry and configured and disposed to receive and detect x-rays from the x-ray source, the detector arrays being displaced relative to each other, in the direction of travel, by an array spacing distance such that a geometric efficiency of the arrays is less than about 80%; and
   a processor coupled to the conveyor and the gantry to control the conveyor and move the object through the housing at a first speed, and to control the rotation of the gantry at a second speed, such that the object will move a distance substantially equal to the array spacing distance during a time the gantry rotates an angle approximately equal to 180° divided by a quantity of detector arrays.

2. The scanner of claim 1 wherein the array spacing distance is such that a geometric efficiency of the arrays is less than about 70%.

3. The scanner of claim 1 wherein the array spacing distance is such that a geometric efficiency of the arrays is less than about 60%.

4. The scanner of claim 1 wherein the array spacing distance is such that a geometric efficiency of the arrays is less than about 50%.

5. The scanner of claim 1 wherein the array spacing distance is such that a geometric efficiency of the arrays is less than about 40%.

6. The scanner of claim 1 wherein the array spacing distance is such that a geometric efficiency of the arrays is less than about 30%.

7. The scanner of claim 1 wherein the array spacing distance is such that a geometric efficiency of the arrays is less than about 20%.

8. The scanner of claim 1 wherein the processor is further configured to knit data received from the plurality of detector arrays into one effective array.

9. A computed tomography scanner comprising:
   a housing;
   a conveyor disposed at least partially within the housing and configured to move an object to be scanned through the housing along a direction of travel;
   an x-ray transmission and detection system connected to the housing and configured and disposed to transmit a plurality of x-ray fan beams through the object on the conveyor with x-rays displaced along the length of travel passing through the object, the x-ray transmission and detection system being further configured to detect x-rays in the plurality of fan beams after passing through the object, the detected x-rays being displaced along the direction of travel when passing through the object; and a processor configured to excite the plurality of fan beams sequentially;

wherein the detected x-rays passing through the object are displaced relative to each other in the direction of travel to provide an effective geometric efficiency of the detected x-rays that is less than about 80%.

10. The scanner of claim 9 wherein the transmission and detection system comprises at least two sources and at least one detector array.

11. The scanner of claim 9 wherein the transmission and detection system comprises at least one detector array with detectors disposed substantially completely 360° around the conveyor.

12. The scanner of claim 9 wherein the transmission and detection system comprises a plurality of x-ray sources disposed substantially completely 360° around the conveyor.

13. The scanner of claim 9 wherein the transmission and detection system comprises detectors having detector widths and a plurality of pairs of x-ray sources with sources in the pairs being displaced relative to each other approximately one-half of the detector width in a direction substantially perpendicular to the direction of travel.

14. The scanner of claim 9 wherein the transmission and detection system is configured such that the effective geometric efficiency is less than about 60%.

15. The scanner of claim 9 wherein the transmission and detection system is configured such that the effective geometric efficiency is less than about 40%.

16. The scanner of claim 9 wherein the transmission and detection system is configured such that the effective geometric efficiency is less than about 20%.

17. The scanner of claim 9 wherein the x-ray transmission and detection system includes a plurality of x-ray sources and the x-ray transmission and detection system is configured to trigger the sources at a plurality of different energies to capture multi-energy data for atomic number calculations.

18. A method of CT scanning an object, the method comprising:

moving the object along a direction of travel;

transmitting displaced x-rays through the object substantially perpendicular to the direction of travel;

detecting the displaced x-rays with an effective geometric efficiency at the object of about 80% or less, wherein the speed at which the object is moved is dependent upon the geometric efficiency and the rate at which the displaced x-rays are detected;

combining information indicative of detected intensities of the displaced x-rays to group information from different x-rays for common slices together;

analyzing the combined information for slices of the object; and outputting at least one result based on the combined information.

* * * * *